(12) United States Patent
Sheu et al.

(10) Patent No.: US 7,150,887 B2
(45) Date of Patent: Dec. 19, 2006

(54) HERBAL PHARMACEUTICAL COMPOSITIONS FOR PROPHYLAXIS AND/OR TREATMENT OF CARDIOVASCULAR DISEASES AND THE METHOD OF PREPARING THE SAME

(75) Inventors: Shuenn-Jyi Sheu, Taipei (TW); Chung Guang Shen, Foster City, CA (US)

(73) Assignee: Sun Ten Phytotech Co., Ltd., Taipei County (TW)

( * ) Notice: Subject to any disclaimer, the term of this patent is extended or adjusted under 35 U.S.C. 154(b) by 0 days.

(21) Appl. No.: 10/875,812

(22) Filed: Jun. 25, 2004

(65) Prior Publication Data

US 2004/0234627 A1 Nov. 25, 2004

Related U.S. Application Data

(62) Division of application No. 10/164,568, filed on Jun. 10, 2002, now Pat. No. 6,793,944.

(30) Foreign Application Priority Data

Dec. 21, 2001 (TW) ............................... 90131897 A

(51) Int. Cl.
*A61K 36/00* (2006.01)
(52) U.S. Cl. .................. 424/725; 424/728; 424/756

(58) Field of Classification Search ............... 424/725, 424/728, 756
See application file for complete search history.

(56) References Cited

U.S. PATENT DOCUMENTS

| 5,318,798 | A | * | 6/1994 | Uchida et al. ......... 427/213.35 |
| 5,443,839 | A | | 8/1995 | Meybeck |
| 6,274,177 | B1 | | 8/2001 | Wu et al. |
| 6,340,480 | B1 | | 1/2002 | Duckett et al. |

OTHER PUBLICATIONS

Yokozawa et al. Effects on the Proliferation of Smooth Muscle Cells of Oriental Medical Prescriptions Used for the Treatment of Ateriosclerosis; Natrual Medicines 50(1), 1996, pp. 9-13.*

* cited by examiner

*Primary Examiner*—Patricia Leith
(74) *Attorney, Agent, or Firm*—Fish & Richardson P.C.

(57) ABSTRACT

The present invention provides an herbal pharmaceutical compositions comprising the root of scutellaria, the rhizome of coptis, the root and rhizome of rhubarb, and the dry powders of the root of ginseng (or American ginseng) or the rhizome of ginger. The herbal pharmaceutical compositions are effective in preventing patients from developing or treating patients with cardiovascular diseases, which include, but are not limited to, hypertension, coronary heart disease, cerebrovascular disease, peripheral vascular disease, heart failure, rheumatic heart disease, congenital heart disease, and cardiomyopathies. The present invention also provides methods for preparing and using the herbal pharmaceutical compositions.

3 Claims, 9 Drawing Sheets

COX-2 iNOS

HERBAL PHARMACEUTICAL COMPOSITIONS FOR PROPHYLAXIS AND/OR TREATMENT OF CARDIOVASCULAR DISEASES AND THE METHOD OF PREPARING THE SAME

RELATED APPLICATIONS

The present application is a Divisional Application of U.S. patent application Ser. No. 10/164,568, filed on Jun. 10, 2002 and now issued as U.S. Pat. No. 6,793,944, which in turn claims the priority to Taiwanese application number 90131897, filed on Dec. 21, 2001, which are herein incorporated by reference.

FIELD OF THE INVENTION

The present invention relates to herbal pharmaceutical compositions which contain the root of scutellaria (Radix Scutellariae), the rhizome of coptis (Rhizoma Coptidis), the root and rhizome of rhubarb (Radix et Rhizoma Rhei), and the root of ginseng (Radix Ginseng) or American ginseng (Radix Panacis Quinquefolii) for prophylaxis or treatment of cardiovascular diseases. Optionally, the root of ginseng or American ginseng can be replaced with the rhizome of ginger (Rhizoma Zingiberis). The herbs can be prepared as dry powders or extracts. The present invention also relates to the methods of preparing and using the herbal pharmaceutical compositions.

BACKGROUND OF THE INVENTION

Based on data from the World Health Organization (WHO), cardiovascular diseases contribute to a third of global deaths in 1999 and are estimated to be the leading cause of death in developing countries by 2010. Cardiovascular diseases are the name for a group of disorders in the heart and blood vessels, including, but not limited to, hypertension (high blood pressure), coronary heart disease (heart attack), cerebrovascular disease (stroke), peripheral vascular disease, heart failure, rheumatic heart disease, congenital heart disease, and cardiomyopathies.

Hypertension is by far the most prevalent cardiovascular disease. It is estimated that more than a third of Americans aged 45 or older have high blood pressure and, among them, more than 50% are aged 60 or older. Untreated hypertension can lead to serious and life-threatening complications, e.g., stroke, coronary heart disease, arteriosclerosis, atherosclerosis, heart failure, kidney failure and blindness.

As indicated in the United States Sixth Report of the Joint National Committee (JNC VI) on High Blood Pressure, current treatment for hypertension includes diuretics, α-blockers, β-blockers, calcium channel blockers, ACE inhibitors, and angiotensin antagonists. These agents can be used as monotherapy or in combination. However, most of these agents ameliorate the symptoms but not curing the diseases. These agents are also frequently accompanied with side effects.

One of the major mechanisms for causing human hypertension is the dysfunction of endothelium. Endothelium is the layer of epithelial cells that lines the cavities of the heart and of the blood and lymph vessels. Its main role is to modulate both vascular tone and structure by producing vasodilator and vasoconstrictor mediators.

When activated by specific agonists such as acetylcholine, endothelial cells produce nitric oxide ("NO"), a labile substance derived by L-arginine degradation through the activity of the endothelial NO synthase ("eNOS"). NO is a powerful relaxing agent which also inhibits platelet aggregation and smooth muscle cell proliferation.

Under pathological conditions, such as hypertension or aging, agonist-induced stimulation of endothelium leads to activation of a cyclooxygenase pathway and consequent production of cyclooxygenase-dependent factors, including thromboxane $A_2$ or prostaglandin $H_2$, or free radicals (such as superoxide anions). Dysfunctional endothelium can also cause vascular damage, in particular, atherosclerosis.

There are two isoforms of cyclooxygenase, cyclooxygenase 1 and 2 (COX-1 and COX-2), also referred to as prostaglandin endoperoxide synthase 1 and 2, which are key enzymes in the conversion of arachidonic acid to prostaglandins, thromboxanes and other eicosanoids. It is believed that COX-1 and COX-2 have different physiologic functions due to striking differences in their tissue expression and regulation. COX-1 is a constitutive enzyme that is present at all times in the body and is responsible for the production of cytoprotective prostaglandins important for homeostatic functions, such as maintaining the integrity of the gastric mucosa, mediating normal platelet function, and regulating renal blood flow. In contrast, COX-2 is a rapidly inducible form of cyclooxygenase that leads to the production of proinflammatory prostaglandins. While COX-2 expression is highly restricted under basal conditions, it is dramatically up-regulated during inflammation. The involvement of COX-2 and the elevated production of prostaglandins are associated with a variety of diseases and disorders, such as brain ischemia and cancers, as well as diseases and disorders in which elevated levels of NO is present.

NO modulates the activity of COX-2 and participates in inflammatory and autoimmune-mediated tissue destruction. The effect of NO on COX-2 is dose-dependent. Low levels of NO activate COX-2. In contrast, large amounts of NO produced by inducible nitric oxide synthase ("iNOS") can inhibit the induction of COX-2 and suppress the formation of COX-2 metabolites.

iNOS is expressed in the myocardium after myocardial infarction (MI) and in heart failure. Myocardium is the middle and thickest layer of the heart wall composes of cardiac muscle. Upregulation or overexpression of iNOS is associated with mild inflammatory cell infiltrate, cardiac fibrosis, hypertrophy, and dilatation. Cardiac hypertrophy is a significant risk factor for the development of congestive heart failure (CHF). Overexpression of iNOS results in overproduction of NO, causing myocardial dysfunction and CHF.

CHF is a form of heart disease in which weakened heart function exists with concomitant edema. CHF has many different causes, including narrowing of the arteries supplying blood to the heart muscle (coronary heart disease), prior heart attack (myocardial infarction) resulting in scar tissue large enough or located so to interfere with normal electrocardiac function, high blood pressure, etc. CHF is one of the most serious cardiovascular diseases affecting adults. Over 4 million people have CHF and the incidence is on the rise. The incidence of this disease or condition is increasing with the aging of the population and is currently the most common cause for hospital admission in the elderly. The total U.S. healthcare expenditure on CHF is over five billion dollars per year.

Atrial fibrillation (AF) is atrial arrhythmia characterized by rapid randomized contractions of the atrial myocardium, causing a totally irregular, often rapid ventricular rate. AF may persist due to structural changes in the atria that are promoted by inflammation. C-reactive protein (CRP) is a marker of systemic inflammation which predicts cardiovascular events and stroke, a common sequela of AF. CRP also induces adhesion molecule expression by endothelial cells.

While a panacea has been hunted for in western medicine for years, researchers turn to traditional Chinese herbal medicine for medications of various diseases. Chinese herbal medicine has existed and been use for treating various diseases for thousands of years.

For example, San-Huang-Hsie-Hsin-Tang is an ancient herbal decoction which was first described in Chin-Kuei-Yao-Lueh (translated into English as "the Prescriptions From the Golden Chamber") for "purging fire and clearing the three torsos" and wherefore it is indicated for insufficient cardiac "Chi," hematemesis, and epistaxis. The decoction is made of equal amounts of the root of scutellaria (Radix Scutellariae), the rhizome of coptis (Rhizoma Coptidis), and the root and rhizome of rhubarb (Radix et Rhizoma Rhei). The decoction has a bitter taste and with a cold nature. The decoction is intended for patients with congestion, flush up, fidgets, shoulder stiffness, gastric obstructive depression, constipation, and forceful pulse. However, the decoction is contraindicated for not suitable for patients with symptoms of prolonged bleeding, marked anemia, and minute-weak pulses.

U.S. Pat. No. 5,443,839 discloses a composition having anti-inflammatory, anti-allergic or anti-aging activity comprising, inter alia, an extract of *Scutellaria*. There is no indication that the composition is effective in treating cardiovascular disease and hypertension.

U.S. Pat. No. 6,274,177 discloses a method of preparing an extract from *Zingiber officinale*, which is potent in anti-inflammation and anti-platelet aggregation. There is no indication that the herbal composition is effective in treating cardiovascular disease and hypertension.

U.S. Pat. No. 6,340,480 discloses a composition and method for treating circulatory conditions including hypertension by promoting systemic vascular relaxation and dilation. The composition is a natural combination of L-arginine, ginseng, and *Zizyphi fructus* in an orally or topically administered form. The combination works synergistically to synthesize NO and thereby promote systemic vascular relaxation and dilation. The combined constituents may work to maintain a critical threshold level of NO in areas that cannot themselves produce it, thereby promoting systemic vascular relaxation and dilation in order to reduce hypertension. However, it is not clear whether the herbal composition is effective in treating cardiovascular disease.

In the invention to be presented in the following section, an herbal pharmaceutical composition is described. This herbal pharmaceutical composition is effective in both prophylaxis and treatment of cardiovascular diseases. The composition is also non-toxic and thus can be used by patients in all ages and physical conditions, including the week, the early and the debilitated.

In addition, the herbal pharmaceutical composition of the present invention provides multiple mechanisms of pharmacologically effects, including lowering and stabilization of blood pressure; inhibition of expression of iNOS; inhibition of COX-2 activity; reduction of blood CRP; and reduction of blood cholesterol.

SUMMARY OF THE INVENTION

The present invention provides herbal pharmaceutical compositions which contain Radix scutellariae (root of scutellaria); Rhizoma Coptidis (rhizome of coptis); Radix et Rhizoma Rhei (root and rhizome of rhubarb); and Radix Ginseng (root of ginseng) or Radix Panacis Quinquefolii (American ginseng). The preferred weight ratio of the root of scutellaria, the rhizome of coptis, the root and rhizome of rhubarb, and the root of ginseng or American ginseng is about 1–2:1–2:1–2:1–2; and most favorably 1:1:1:1. Optionally, the root of ginseng or American ginseng can be replaced with Rhizoma Zingiberis (rhizome of ginger). The preferred weight ratio of the root of scutellaria, the rhizome of coptis, the root and rhizome of rhubarb, and the rhizome of ginger is about 1–2:1–2:1–2:1–2; and most favorably 1:1:1:1.

The herbs of the present invention can be prepared in the form of dry powders or extracts. The herbal pharmaceutical composition containing dry powders of the root of scutellaria, the rhizome of coptis, the root and rhizome of rhubarb, and the root of ginseng or American ginseng (as shown in Example 1, infra) is pharmaceutically active and possesses the properties of lowering and maintaining blood pressure as well as treating other cardiovascular diseases. However, the preferred pharmaceutical compositions of the present invention are the ones containing a mixture of both herbal extracts and dry powders. Preferably, the root of scutellaria, the rhizome of coptis, and the root and rhizome of rhubarb are prepared as extracts, where the active ingredients of the herbs are extracted by a solvent, which can be water, alcohol, or a mixture thereof. The preferred solvent for the root of scutellaria and the rhizome of coptis is water. The preferred solvent for the root and rhizome of rhubarb is alcohol, most favorably 95% alcohol (in water).

The preferred form of ginseng/American ginseng or ginger used in the herbal pharmaceutical compositions is dry powders, which are prepared by cutting and grinding the herbs, followed by drying.

In addition to the herbs, the herbal pharmaceutical compositions of the present invention can contain a pharmaceutically acceptable excipient and/or carrier and be formulated in various dosage form such as granule, capsule, tablet, powder, and bolus, for orally administration. The preferred formulation is tablet.

The present invention provides a methods for preparing the herbal pharmaceutical compositions which contain a mixture of herbal extracts and dry powders as follows: (1) individually extracting the root of scutellaria, the rhizoma of coptis, and the root and rhizome of rhubarb with an appropriate solvent to form respective extracts of the herbs; (2) individually filtering the respective extracts of the herbs; (3) mixing the respectively filtered extracts of the herbs to form an herbal mixture; (4) condensing the herbal mixture to form an herbal paste; (5) grinding the root of ginseng or American ginseng to make dry powders of ginseng or American ginseng; (6) adding the dry powders of ginseng or American ginseng to the herbal paste; and (7) drying the paste to form the herbal pharmaceutical compositions.

Optionally, the root of ginseng or American ginseng can be replaced with Rhizoma Zingiberis (rhizome of ginger).

The root of scutellaria and the rhizome of coptis are preferably extracted by water. The root and rhizome of rhubarb can either be extracted by alcohol or by a mixture of alcohol and water, preferably 95% alcohol in water.

The herbal pharmaceutical composition of the present invention has therapeutic effect on cardiovascular diseases and can be used for prevention and/or treatment of cardiovascular diseases, including, but not limited to, hypertension, coronary heart disease, cerebrovascular disease, peripheral vascular disease, heart failure, rheumatic heart disease, congenital heart disease, and cardiomyopathies.

Specifically, the herbal pharmaceutical composition of the present invention can stabilize and lower blood pressure, prevent damage to endothelial cell (e.g., by inhibiting iNOS activity, inhibiting COX-2 activity, reducing blood CRP concentration, inhibiting smooth muscular cell proliferation, and reduce blood cholesterol level). The herbal pharmaceutical composition can be safely used by patients at any ages and physical conditions, including the weak, the elderly, and the debilitated.

DETAILED DESCRIPTION OF THE INVENTION

Figure 1:
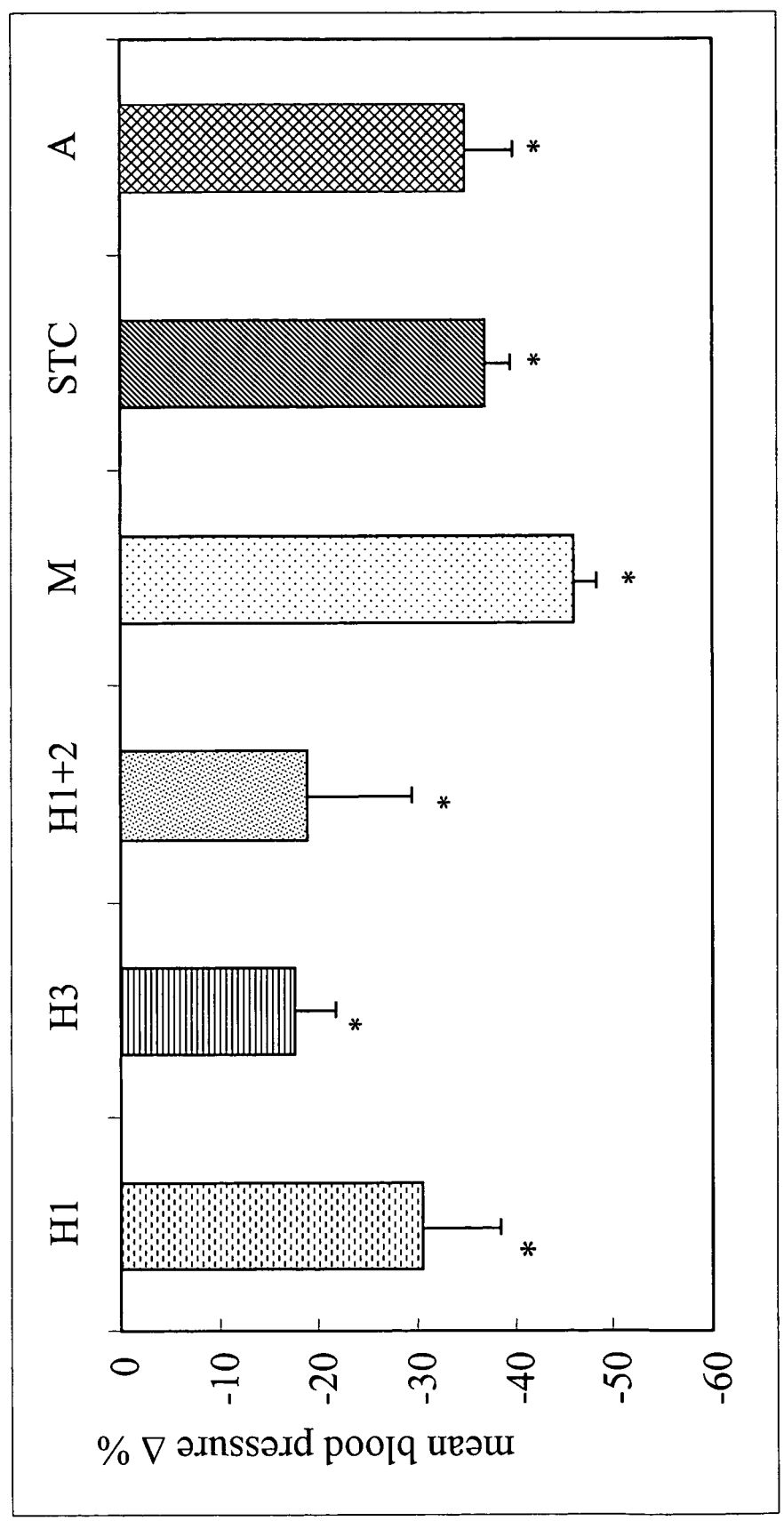
FIG. 1 shows the anti-hypertensive effects of: (1) the root of scutellaria alone (H1); (2) the root and rhizome of rhubarb alone (H3); (3) a combination of the root of scutellaria and the rhizome of coptis (H1+2); (4) the modified San-Huang-Hsie-Hsin-Tang decoction (M) as shown in COMPARATIVE EXAMPLE 1, infra; (5) STC (Example 3), infra; and (6) a combination of captopril and nifedipine (A) in rats. Captopril is an ACE inhibitor. Nifedipine is a calcium channel blocker. * indicates statistical significance.

The present invention provides novel herbal pharmaceutical compositions for preventing and treating cardiovascular diseases, which are suitable for patients of all age groups and physical conditions, including elderly and debilitated.

Recent progress in the scientific and medical understanding of the cardiovascular diseases provide more knowledge on the involvement of endothelial damages, nitric oxide (NO), inflammation reactions and C-reactive protein (CRP) in these diseases. NO produced in the endothelium by the endothelial nitric oxide synthase (eNOS) is not only a potent vasodilator but also inhibits platelet aggregation, smooth muscle cell proliferation, monocyte adhesion and adhesion molecule expression, thus, maintain the integrity of the endothelial tissues. Production of cyclooxygenase (COX)-dependent factors, including prostanoids and oxygen free radicals, may be the main cause for endothelial dysfunction. Dysfunctional endothelium can then be one of the main mechanisms causing vascular damage which can further lead to more severe cardiovascular diseases. As inhibition of cyclooxygenase may restore NO-mediated vasodilation in essential hypertension, anti-inflammatory interventions may have therapeutic utility.

During diseased states, e.g., cardiac hypertrophy, myocardial infarction (MI), ischemia, myocarditis and septic shock, overexpression of the inducible nitric oxide synthase (iNOS) leads to increased production of NO. The elevated NO levels can result in more severe complications, e.g., myocardial dysfunction, congestive heart failure and sudden cardiac death.

During the inflammation process, an acute-phase reactant, C-reactive protein (CRP), is formed. CRP, frequently used as a systemic inflammation marker, promotes the expression of the adhesion molecules and may plays a direct role in the pathogenesis of vascular inflammation, particularly atherosclerosis. CRP has been associated with vascular risk factors and with prevalent and incident atherothrombotic cardiovascular diseases, i.e., coronary heart disease, stroke, and peripheral arterial disease.

A new approach for treatment of cardiovascular diseases should consider all aspects of the diseases. For example, in addition to the anti-hypertensive activity, the new medicine should not only be able to protect healthy endothelium but also improve the functions of dysfunctional endothelium.

The present invention provides herbal pharmaceutical compositions that have the functions of reducing high blood pressure, maintaining normal blood pressure, improving and protecting cardiovascular endothelial cell functions, so as to treat and prevent cardiovascular diseases.

The herbal pharmaceutical compositions of the present invention contain four herbs: the root of scutellaria, the rhizome of coptis, the root and rhizome of rhubarb, and the root of ginseng or American ginseng. Optionally, the root of ginseng or American ginseng can be replaced with the rhizome of ginger.

The herbs used in the compositions can be any variants of the herbs mentioned above. For example, the root of scutellaria has three closely related variants, which are, *Scutellaria baicalensis* Georgi, *Scutellaria viscidula* Bge., and *Scutellaria amoena* C. H. Wright. The rhizome of coptis has four closely related variants, which are, *Coptis chinensis* Franch., *Coptis deltoidea* C. Y. Cheng et Hsiao, *Coptis teetoides* C.Y. Cheng, and *Coptis omeiensis* (Chen) C.Y. Cheng. The root and rhizome of rhubarb has three closely related variants, which are *Rheum palmatum* L., *Rheum tanguticum* Maxim., and *Rheum officinale* Baill.

The pharmaceutical effect of scutellaria is in the dried root, which has the pharmaceutical name of Radix Scutellariae. *Scutellaria* belongs to the family of Labiatae. The herb is mainly produced in the provinces of Hebei, Shanxi, and inner Mongolia of China. The best harvest seasons for the herb are in spring or autumn. The root of scutellaria is dried under the sunlight, sliced, and used unprepared or stir-baked with wine or stir-baked to charcoal. The herb is bitter in flavor and cold in property. According to traditional Chinese medicine, the herb can be used to cure diseases in lung, gallbladder, stomach, and large intestine channels. Specifically, the herb can be used to remove damp-heat, counteract toxicity, arrest bleeding, and prevent abortion in patients.

The root of scutellaria contains active ingredients which include, but are not limited to, baicalin, oroxylin A-glucuronide, wogonin-7-O-glucuronide, baicalein, wogonin, and oroxylin A. Baicalin can be used as a denominator for qualitative or quantitative control of the herb.

The pharmaceutical effect of coptis is in the dried rhizome of coptis, which has the pharmaceutical name of Rhizoma Coptidis. *Coptis* belongs to the family of Ranunculaceae. It is mainly produced in the provinces of Sichuan, Hubei, and Yunnan of China. The preferred harvest season is in autumn. The rhizome of coptis is dried under the sunlight after the rootlets and earth have been removed and used unprepared or stir-baked with ginger juice. The herb is bitter in flavor and cold in property. According to traditional Chinese medicine, the herb can be used to cure diseases in the heart, stomach, liver, and large intestine channels.

The rhizome of coptis contains active ingredients, which include, but are not limited to, berberastine, columbamine, jatrorrhizine, epiberberine, coptisine, palmatine, and berberine. Berberine can be used as a denominator for the qualitative or quantitative control of the herb.

The pharmaceutical effect of rhubarb is in the dried root and rhizome of rhubarb, which has the pharmaceutical name of Radix et Rhizoma Rhei. Rhubarb belongs to the family of Polygonaceae. It is mainly produced in the provinces of Qinghai and Sichuan of China. The root and rhizome of rhubarb is dug in the late autumn when its stem and leaves begin to wither, or in the early spring before the plant begins to sprout. The harvested herb is dried and sliced. The root and rhizome of rhubarb can be used unprepared, stir-baked with wine, or carbonized. It is bitter in flavor and cold in property. According to traditional Chinese medicine, the root and rhizome of rhubarb can cure diseases in spleen, large intestine, liver, and heart channels.

The root and rhizome of rhubarb contains active ingredients, which include, but are not limited to, sennoside B, sennoside A, aloe-emodin, rhein, emodin, and chrysophanol. Sennoside A and/or emodin can be used as denominators for qualitative or quantitative control of the herb.

There are two kinds of ginseng, Radix Ginseng (root of ginseng) and Radix Panacis Quinquefolii (root of American ginseng), which can be used in the herbal pharmaceutical composition of the present invention. Radix Ginseng is *Panax ginseng* C. A. Mey. Radix Panacis Quinquefolii is *Panax quinquefollum* L. Radix Ginseng belongs to the family of Araliaceae. Ginseng is mainly produced in the provinces of Jilin, Liaoning, and Heilongjiang of China. Ginseng produced in Fusong of Jilin is particularly of good quality. The herb can also be cultivated, which is called "garden ginseng," as opposed to "mountain ginseng" which refers to the ginseng found in the wild. Cultivated ginseng is harvested in autumn. The harvested ginseng is dried in the sun or roasted, which is called "sun-dried ginseng," or dried after being steamed, which is called "red ginseng," or soaked in syrup, which is known as "sugar-processed ginseng." The fibrous rootlets are known as ginseng rootlets. Wild ginseng dried in the sun is known as sun-cured wild ginseng. The herb is sliced for use. The herb has a sweet and slightly bitter flavor and is neutral in property. According to traditional Chinese medicine, ginseng is particularly good for curing diseases in spleen, lung, and heart channels.

The pharmaceutical effects of ginseng are in its dried root. Ginseng also has effects on central nervous system. It enhances both stimulatory and inhibitory processes in the central nervous system, thereby improving the adaptability of nervous responses. Ginseng can also lower serum glucose and cholesterol. It also shows therapeutic and preventive effect on peptic ulcer.

Radix Panacis Quinquefolii also known as American ginseng, belongs to the family of Araliaceae. The medicinal effects of American ginseng is in the root. American ginseng can be found in northern United States and Canada. It has also been widely cultivated in France and northern China. The best harvest season for American ginseng is in autumn.

The active ingredients in the root of ginseng or American ginseng include, but are not limited to, ginsenoside Rg1, ginsenoside Re, and ginsenoside Rb1, among which ginsenoside Rb1 can be used as a denominator for qualitative or quantitative control of the herb.

The pharmaceutical effect of ginger is in the dried rhizome of ginger, which has the pharmaceutical name of Rhizoma Zingiberis. Ginger belongs to the family of Zingiberaceae. Fresh rhizome or dried rhizome of ginger can be prepared by baking, roasting, and simmering. Ginger can be found throughout China, especially Sichuan, Guizhou, Guangdong. It is primarily cultivated. The best season for harvest is before the winter solstice. Ginger is acrid and has warm property. According to traditional Chinese medicine, ginger is particularly good for curing diseases in spleen, lung, and stomach.

The active ingredients in the rhizome of ginger include, but are not limited to, gingerol, shogaol, and zingerone, among which gingerol can be used as a denominator for qualitative and quantitative control of the herb.

The pharmaceutical names, botanical or zoological names, family names, common descriptions, and major ingredients of the herbs used in the present invention are shown in Table 1.

TABLE 1

Herbs of the Present Pharmaceutical Composition

| Pharmaceutical Name | Botanical Name | Family | Common Description | Major Ingredients |
|---|---|---|---|---|
| Radix Scutellariae | Scutellaria baicalensis Georgi | Labiatae | scutellaria or scute | baicalein, baicalin, wogonin, wogonin-7-0-glucuronide, neobaicalein, oroxylin A glucuronide, camphesterol, β-sitosterol, benzoic acid |
| Rhizoma Coptidis | Coptis chinensis Franch., C. deltoidea C. Y. Cheng, C. omeiensis (Chen) C. Y. Cheng, or C. teetoides C. Y. Cheng | Ranunculaceae | coptis rhizome | berberine, coptisine, worenine, palmatine, columbamine, obacunone, obaculactone, palmatine, jatrorrhizine, magnoflorine, ferulic acid |
| Radix et Rhizoma Rhei | Rheum palmatum L. or R. tanguticum Maxim. et Reg. (used in north China) or R. officinale Baill. (used in south China) | polygonaceae | rhubarb root and rhizome | derivatives of anthraquinone glycosides including chrysophanol, emodin, aloe-emodin, rhein, and physcion, rheum tannic acids, gallic acid, catechin, tetrarin, glucogallin, cinnamic acid, rheosmin, fatty acids, calcium oxalate, glucose, fructose, sennoside A, B, and C |
| Rhizoma Zingiberis | Zingiber officinale Roscoe | Zingiberaceae | ginger, ginger rhizome | gingerol, shogaol, and zingerone |
| Radix Panacis Quinquefolii | Panax quinquefolium L. | Araliaceae | American ginseng | saponins, panaquilon |
| Radix Ginseng (Rubra) | Panax ginseng C. A. Mey | Araliaceae | ginseng, red ginseng | panaxatriol, panaxadiol, other panoxisides, panoquilon, panaxin, ginsenin, α-panaxin, protopanaxadiol, protopanaxtriol, panacene, panaxynol, panaenic acid, panose, dammarane, glucose, fructose, maltose, sucrose, nicrotinic acid, riboflavin, thiamine |

In the pharmaceutical compositions of the present invention, the root of scutellaria, the rhizome of coptis, and the root and rhizome of rhubarb are best prepared by solvent extraction. The solvent can be water or any pharmaceutically acceptable organic solvent or a mixture of water and the organic solvent. The organic solvent is preferred to be alcohol.

In the pharmaceutical composition of the present invention, the weight ratio of the root of scutellaria, the rhizome of coptis, the root and rhizome of rhubarb, and the root of ginseng or American ginseng is about 1–2:1–2:1–2:1–2, most favorably 1:1:1:1.

Optionally, the rhizome of ginger can replace the root of ginseng or American ginseng.

The pharmaceutical compositions of the present invention can be formulated into tablet, bolus, powder, capsule, and granule by means suitable and known in the art and the pharmaceutical industry. The preferred formulation is tablet.

Quality Control of the Herbs

The present invention uses High Performance Liquid Chromatography (HPLC) to fingerprint each herb for the purpose of ensuring quality of individual herbal ingredients. The HPLC method and the test results of the herbal components of the present invention are described as follows:

A. Preparation of Herbal Extracts for HPLC
  (1) 0.5 gram of the herbal component was precisely weighed and placed in a 50-mL sample bottle.
  (2) 20 mL of 70% methanol was added to the sample bottle of (1).
  (3) The mixture of (2) was sonicated at room temperature for 15 minutes and further shaken in a 40° C. water bath at 160 rpm for 20 minutes; the sample was then sat for 30 minutes or more until two layers of the solution was formed.
  (4) The clear, upper layer of the solution was taken out and passed through a 0.45 μm PVDF filter made by Whatman, England.
  (5) About 20 μL of the filtered solution was injected into the HPLC for quantitative analysis.

B. Instruments for HPLC Analyses
  The instruments used include Waters 600E Pump, Waters 717Plus Autosampler, and Waters 996 Photodiode Array Detector.

C. HPLC Conditions and Results of Individual Herbs
  1. Rhubarb
    (a) HPLC Conditions:
      Guard column: Lichrospher RP-18 endcapped
        (5 μm, 4.0 ID×10 mm, Merck, German)
      Column: Symmetry Shield RP 18
        (5 μm, 4.6 ID×250 mm, Waters, USA)

Column temperature: 40° C.
Mobile phase: A: 0.5% acetic acid (CH$_3$COOH) in water
 B: acetonitrile (CH$_3$CN)
Elution Gradients:

| Time (minutes) | A (%) | B (%) | Linearity |
|---|---|---|---|
| 0 | 86 | 14 | * |
| 40 | 75 | 25 | linear |
| 60 | 55 | 45 | linear |
| 70 | 55 | 45 | linear |
| 90 | 0 | 100 | linear |
| 100 | 86 | 14 | linear |

Flow rate: 0.85 mL/min
Detection wavelength: 270 nm
(b) Results:
The HPLC chromatogram of the root and rhizome of rhubarb contains the indicative ingredients of sennoside B, sennoside A, aloe-emodin, rhein, emodin, and chrysophanol. The retention times and maximum absorption wavelengths of these ingredients are shown in Table 2.

TABLE 2

Retention Times and Wavelengths of the Ingredients in Rhubarb

| Compound | Retention Time (minutes) | Maximum absorption wavelength ($\lambda$max) |
|---|---|---|
| Sennoside B (SB) | ~38 | 268 nm |
| Sennoside A (SA) | ~46 | 269 nm |
| Aloe-emodin (AL) | ~72 | 277 nm |
| Rhein (RH) | ~87 | 257 nm |
| Emodin (EM) | ~92.5 | 287 nm |
| Chrysophenol (CH) | ~94 | 256 nm |

2. *Scutellaria*
 (a) HPLC Conditions:
 Guard column: Lichrospher RP-18 endcapped
  (5 μm, 4.0 ID×10 mm, Merck, German)
 Column: Cosmosil 5C18-MS
  (5 μm, 4.6 ID×250 mm, Nacalai tesque, Japan)
 Column temperature: 35° C.
 Mobile phase: A: 20 mM KH$_2$PO$_4$ and 0.01% H$_3$PO$_4$ in water
  B: acetonitrile (CH$_3$CN)
  C: water (H$_2$O)
 Elution Gradients:

| Time (minutes) | A (%) | B (%) | C (%) | Linearity |
|---|---|---|---|---|
| 0 | 87 | 13 | 0 | * |
| 25 | 75 | 25 | 0 | Linear |
| 40 | 65 | 35 | 0 | Linear |
| 55 | 0 | 75 | 25 | Linear |
| 60 | 87 | 13 | 0 | Linear |

Flow rate: 1.0 mL/min
Detection wavelength: 280 nm
(b) Results:
The HPLC chromatogram of the root of scutellaria contains the indicative ingredients of baicalin, oroxylin A-glucuronide, wogonin-7-O-glucuronide, baicalein, wogonin, and oroxylin A. The retention times and maximum absorption wavelengths of these ingredients are shown in Table 3.

TABLE 3

Retention Times and Wavelengths of the Ingredients in Scutellaria

| Compound | Retention Time (minutes) | Maximum absorption wavelength ($\lambda_{max}$) |
|---|---|---|
| Baicalin (BG) | ~30 | 276 nm |
| Oroxylin A-glucuronide (OG) | ~36 | 269 nm |
| Wogonin-7-O-glucuronide (WG) | ~39 | 272 nm |
| Baicalein (B) | ~51 | 275 nm |
| Wogonin (W) | ~56 | 274 nm |
| Oroxylin A (O) | ~57 | 269 nm |

3. *Coptis*
 (a) HPLC Conditions
 Guard column: Lichrospher RP-18 endcapped
  (5 μm, 4.0 ID×10 mm, Merck, German)
 Column: Cosmosil 5C18-MS
  (5 μm, 4.6 ID×250 mm, Nacalai tesque, Japan)
 Column temperature: 35° C.
 Moble phase: A: buffered acetonitrile (The buffer contains 50 mM of CH$_3$COONa, 2% CH$_3$COOH, and 5 mM C$_{12}$H$_{25}$OSO$_3$Na)
  B:H$_2$O:CH$_3$CN:CH$_3$OH=10:45:45 (v/v)
 Elution Gradients:

| Time (minutes) | A (%) | B (%) | Linearity |
|---|---|---|---|
| 0 | 100 | 0 | * |
| 15 | 65 | 35 | linear |
| 30 | 65 | 35 | linear |
| 40 | 100 | 0 | linear |

Flow rate: 0.85 mL/min
Detection wavelength: 270 nm
(b) Results:
The HPLC chromatogram of the rhizome of coptis contains the indicative ingredients of berberastine, columbamine, jatrorrhizine, epiberberine, coptisine, palmatine, and berberine. The retention times and maximum absorption wavelengths of these ingredients are shown in Table 4.

TABLE 4

Retention Times and Wavelengths of the Ingredients in Coptis

| Compound | Retention Time (minutes) | Maximum absorption wavelength ($\lambda$max) |
|---|---|---|
| Berberastine (Berber) | ~17 | 264 nm; 357 nm |
| Columnbamine (Col) | ~21 | 264 nm; 345 nm |
| Jatrorrhizine (Jat) | ~21.5 | 264 nm; 345 nm |
| Epiberberine (Epi) | ~22.5 | 267 nm; 357 nm |
| Coptisine (Cop) | ~23.5 | 264 nm; 358 nm |
| Palmatine (Pal) | ~26 | 272 nm; 345 nm |
| Berberine (Ber) | ~27 | 263 nm; 347 nm |

4. Ginseng
 (a) HPLC Conditions
 Guard column: Lichrospher RP-18 endcapped
  (5 μm, 4.0 ID×10 mm, Merck, German)
 Column: Cosmosil 5C18-MS
  (5 μm, 4.6 ID×250 mm, Nacalai tesque, Japan)

Column temperature: 35° C.
Mobile phase: A: 20 mM KH$_2$PO$_4$
  B: CH$_3$CN
  C: H$_2$O
Elution Gradients:

| Time (minutes) | A (%) | B (%) | C (%) | Linearity |
| --- | --- | --- | --- | --- |
| 0 | 80 | 20 | 0 | * |
| 20 | 75 | 25 | 0 | Linear |
| 40 | 65 | 35 | 0 | Linear |
| 55 | 0 | 80 | 20 | Linear |
| 60 | 0 | 20 | 80 | Linear |
| 65 | 80 | 20 | 0 | Linear |

Flow rate: 1.0 mL/min
Detection wavelength: 203 nm
(c) Results:
The HPLC chromatogram of the root of ginseng contains the indicative ingredients of ginsenoside R$_{g1}$, ginsenoside Re, and ginsenoside R$_{b1}$. The retention times and maximum absorption wavelengths of these ingredients are shown in Table 5.

TABLE 5

Retention Times and Wavelengths of the Ingredients in Ginseng

| Compound | Retention Time (minutes) | Maximum absorption wavelength (λmax) |
| --- | --- | --- |
| Ginsenoside R$_{g1}$ (R$_{g1}$) | ~23.5 | 204 nm |
| Ginsenoside Re (Re) | ~23.8 | 203 nm |
| Ginsenoside R$_{b1}$ (R$_{b1}$) | ~38.5 | 203 nm |

5. Ginger
 (a) HPLC Conditions
 Guard column: Lichrospher RP-18 endcapped
  (5 μm, 4.0 ID×10 mm, Merck, German)
 Column: Cosmosil 5C$_8$-MS
  (5 μm, 4.6 ID×250 mm, Nacalai tesque, Japan)
 Column temperature: 35° C.
 Mobile phase: A: 20 mM KH$_2$PO$_4$
  B: CH$_3$CN
  C: H$_2$O
 Elution Gradients:

| Time (minutes) | A (%) | B (%) | C (%) | Linearity |
| --- | --- | --- | --- | --- |
| 0 | 70 | 30 | 0 | * |
| 20 | 40 | 60 | 0 | Linear |
| 30 | 0 | 80 | 20 | Linear |
| 35 | 0 | 30 | 70 | Linear |

Flow rate: 1.0 mL/min
Detection wavelength: 280 nm
(d) Results:
The HPLC chromatogram of the rhizome of ginger contains the indicative ingredients of 6-gingerol, and 6-shogaol. The retention times and maximum absorption wavelengths of these ingredients are shown in Table 6.

TABLE 6

Retention Times and Wavelengths of the Ingredients in Ginger

| Compound | Retention Time (minutes) | Maximum absorption wavelength (λmax) |
| --- | --- | --- |
| 6-Gingerol (G) | 17 | 230 nm; 285 nm |
| 6-Shogaol (S) | 26 | 230 nm; 285 nm |

PHARMACEUTICAL COMPOSITIONS

The pharmaceutical compositions of the present invention is prepared by the following procedures:

(1) Preparation of Herbal Extracts
Some of the herbs (e.g., scutellaria, coptis, and rhubarb) are preferred to be individually extracted by a solvent. The solvent can be water or organic solvent that is pharmaceutically acceptable for extraction purpose, or a mixture of water and the organic solvent. The preferred organic solvent is alcohol. It is preferred that the root of scutellaria and the rhizome of coptis are extracted by water, and the root and rhizome of rhubarb is by alcohol, especially 95% of alcohol in water (v/v). The extracts are further filtered.

(2) Condensation of the Herbal Extracts
For the herbs that have been prepared by extraction, the individual herbal extracts, after filtration, are pooled together and condensed under reduced pressure in a water bath (maintained at 50° C.) until an herbal paste is formed.

(3) Preparation of Dry Powders
All of the herbs used in the herbal pharmaceutical compositions can be used in the form of dry powders. However, for better therapeutic effects, all herbs, except ginseng/American ginseng or ginger, are preferred to be prepared by solvent extraction. As to ginseng/American ginseng or ginger, the dry powders form of the herbs are prepared by cutting the herbs into small pieces, followed by grinding and drying them into powders. The dry powders of the herbs are then passed through a sieve to ensure that the size of the dry powders are within certain ranges.

(4) Preparation of A Herbal Pharmaceutical Composition
The dry powders of the herbs are mixed in with the herbal paste as shown in (2), supra, to form an herbal mixture, which is further dried to form the pharmaceutical composition. Additionally, the pharmaceutical composition can be processed into tablet, bolus, powder, capsule, and granule by means of formulation which is well-known to those ordinary skill in the art, particularly in the pharmaceutical industry. Excipients, binders, carriers, fillers can be added to the herbal mixture.

The following examples are for illustrative purpose and are not intended to limit the scope of the invention. Reasonable variations, such as those understood by reasonable artisans, can be made herein without departing from the scope of the present invention.

EXAMPLE 1

Preparation of Herbal Pharmaceutical Composition 1

Herbal pharmaceutical composition 1 of the present invention was prepared as follows:

(1) About 20 grams of each of the root of scutellaria, the rhizome of coptis, the root and rhizome of rhubarb, and ginseng, in the form of "Yin Pian" (meaning "drinking pieces"), which contained small thin slices of the herb that were ready for decoction use, were individually measured.

(2) The herbs of (1) were individually ground in a grinder into individual powder forms.

(3) The individual powders of (2) were passed though a 120-mesh sieve respectively and the resultant powders were collected.

(4) The individual powders of (3) were mixed together until a homogeneous mixture was obtained.

EXAMPLE 2

Preparation of Herbal Pharmaceutical Composition 2

The herbal pharmaceutical composition 2 of the present invention was prepared as follows:

(1) About 20 grams of each of the root of scutellaria, the rhizome of coptis, and the root and rhizome of rhubarb, in the form of "Yin Pian" (meaning "drinking pieces"), which contained small thin slices of the herb that were ready for decoction use, were individually measured.

(2) The individually measured herbs of (1) were separately simmered and/or boiled in about 20 volumes of water for about 60 minutes to produce individual herbal extracts.

(3) The individually boiled herbal extracts were passed through a 100-mesh sieve when the extracts were still hot; and the filtered extracts were individually collected.

(4) The individually filtered herbs of (3) were mixed together and condensed under condensed pressure in a 50° C. water bath until a paste was formed.

(5) About 20 grams of the dry powders of ginseng or American ginseng were prepared according to (1) and (2) of Example 1, supra.

(6) The herbal paste of (4) and the dry powders of (5) were mixed together until a homogeneous paste was obtained.

EXAMPLE 3

Preparation of Herbal Pharmaceutical Composition 3 (STC)

The herbal pharmaceutical composition 3 of the present invention was prepared as follows (NOTE: The herbal pharmaceutical composition 3 is also known as STC, which is named after "SunTen Cardiovascular Drug"):

(1) About 20 grams of each of the root of scutellaria, the rhizome of coptis, and the root and rhizome of rhubarb, in the form of "Yin Pian" (meaning "drinking pieces"), which contained small thin slices of the herb that were ready for decoction use, were individaully meansured.

(2) The small pieces of scutellaria and coptis were individually simmered and/or boiled in about 20 volumes of water for about 60 minutes to produce the extracts of scutellaria and coptis, respectively.

(3) The extracts of scutallaria and coptis were separately passed through a 100-mesh sieve when the extracts were still hot; and the filtered herbal extracts were individually collected.

(4) The filtered herbal extracts of (3) were mixed together and condensed under reduced pressure in a 50° C. water bath until a paste was formed.

(5) About 20 grams of root and rhizome of rhubarb, in the form of "Yin Pian" were meansured, and extracted under refluxing in about 20 volumes of alcohol: water (95:5, v/v) for 60 minutes to produce a rhubarb extract.

(6) The rhubarb extract of (6) was passed through a 100-mesh sieve; and the filtered rhubarb extract was collected.

(7) The filtered rhubarb extract was condensed under reduced pressure in a 50° C. water bath until a paste was formed.

(8) About 20 grams of dry powders of ginseng or American ginseng was prepared according to (1) and (2) of Example 1, supra.

(9) The dry powders of (8) were mixed with the pastes of (4) and (7) until a homogeneous paste was obtained.

EXAMPLE 4

Preparation of Herbal Composition 4

The herbal pharmaceutical composition 4 of the present invention was prepared using the same procedures as Example 2, except that the root of scutellaria, the rhizome of coptis, and the root and rhizome of rhubarb were extracted in alcohol: water (50:50, v/v), rather than water.

EXAMPLE 5

Preparation of Herbal Pharmaceutical Composition 5

The herbal pharmaceutical composition 5 of the present invention was prepared using the same procedures as in Example 2, except that the root of scutellaria, the rhizome of coptis, and the root and rhizome of rhubarb were extracted in alcohol: water (95:5, v/v).

EXAMPLE 6

Preparation of Herbal Pharmaceutical Composition 6

The herbal pharmaceutical composition 6 of the present invention was prepared using the same procedures as in Example 1, except that ginger was used to replace ginseng or American ginseng.

EXAMPLE 7

Preparation of Herbal Pharmaceutical Composition 7

The herbal pharmaceutical composition 7 of the present invention was prepared using the same procedures as in Example 2, except that ginger was used to replace ginseng or American ginseng.

EXAMPLE 8

Preparation of Herbal Pharmaceutical Composition 8

The herbal pharmaceutical composition 8 of the present invention was prepared using the same procedures as in Example 4, except that ginger was used to replace ginseng or American ginseng.

EXAMPLE 9

Preparation of the Herbal Pharmaceutical Composition 9

The herbal pharmaceutical composition 9 of the present invention was prepared using the same procedures as in Example 4, except that ginger was used to replace ginseng or American ginseng.

EXAMPLE 10

Preparation of Herbal Pharmaceutical Composition 10

The herbal pharmaceutical composition 10 of the present invention was prepared using the same procedures as in Example 5, except that ginger was used to replace ginseng or American ginseng.

COMPARATIVE EXAMPLE 1

Preparation of Modified San-Huang-Hsie-Hsin-Tang

San-Huang-Hsie-Hsin-Tang contains the root of scutellaria, the rhizome of coptis, and the root and rhizome of rhubarb. The commercially available San-Huang-Hsie-Hsin-Tang is a decoction, which contains the "Yin-Pians" (small thin slices) of the root of scutellaria, the rhizome of coptis, and the root and rhizome of rhubarb. When in use, the "Yin-Pians" were placed in a bowl and boiled water was added to the "Yin-Pians"—containing bowl for drink as a soup or a beverage. Alternatively, the "Yin-Pians" of San-Huang-Hsie-Hsin-Tang can be placed in a boiler to be cooked with water.

To properly compare the herbal pharmaceutical compositions of the present invention (i.e., Examples 1–10) with San-Huang-Hsie-Hsin-Tang, the three ingredients of the San-Huang-Hsie-Hsin-Tang were prepared the same way as that in Example 2, i.e., by boiling the "Yin-Pians" of the root of scutellaria, the rhizome of coptis, and the root and rhizome of rhubarb individually in water. The extracts were filtered, combined and then condensed into a paste.

COMPARATIVE EXAMPLE 2

Preparation of Modified San-Huang-Hsie-Hsin-Tang

To properly compare the herbal pharmaceutical compositions of the present invention (i.e., Examples 1–10) with San-Huang-Hsie-Hsin-Tang, the three ingredients of the San-Huang-Hsie-Hsin-Tang were prepared the same way as that in Example 3, i.e., by boiling the "Yin-Pians" of the root of scutellaria and the rhizome of coptis individually in water and extracting the root and rhizome of rhubarb in alcohol: water (95:1, v/v) under refluxing. The extracts of scutellaria and coptis were separately filtered, combined, and condensed into a paste. The extract of rhubarb was filtered and condensed into a paste. The paste of scutellaria and coptis and the paste of rhubarb was then combined and mixed thoroughly.

Pharmacological Studies

The following pharmacological studies confirm that the herbal pharmaceutical compositions of Examples 1–10, supra, were capable of lowering high blood pressure, maintaining stable blood pressure (in the normal range), improving cardiovascular diseases in the elderly, inhibiting the formation of nitrite, inhibiting the proliferation of smooth muscle, reducing CRP formation, inhibiting iNOS expression, and inhibiting COX-2 activity. Such herbal compositions were not only useful for treating patients with normal physique, but also safe and effective for treating patients who were elderly or debilitated.

Although herbal pharmaceutical compositions 1–10, supra, all demonstrated therapeutic effectiveness in treating patients with cardiovascular diseases, Example 3, also known as STC, appeared to be superior to the rest of the Examples. Therefore, for the purpose of simplifying the studies to be presented below, only STC was chosen as representing the pharmaceutical composition of the present invention.

Study 1

Effects of the Herbal Compositions on Lowering Blood Pressure

Spontaneous hypertensive rats (SHR) were obtained from the National Experimental Animal Center, Taiwan. The SHR rats were first anaesthetized by intraperitoneal injection of urethane at 9 g/kg. The SHR rats were then inserted with a trachea tube, maintained on a respiration apparatus for small animals, and inserted with catheters into the femoral vein and femoral artery.

The catheter from the femoral artery was connected to a pressure transducer, which transmitted the change in pressure to a multi-function recorder for monitoring of the artery blood pressure, mean arterial blood pressure, and heart rate. The femoral vein catheter was in place for intravenous injection. The body temperature of the rats was maintained at 37–38° C. by an electric blanket. The baseline values were recorded after the blood pressure of the SHR rats were stabilized.

The SHR rats were separated into six groups and received a single dose of one of the following medications through gavage: (1) 144 mg/kg of the root of scutellaria alone (H1); (2) 144 mg/kg of the root and rhizome of rhubarb alone (H3); (3) 144 mg/kg of the combination of the root of scutellaria and the rhizome of coptis (H1+2); (4) 144 mg/kg of the compositions San-Huang-Hsie-Hsin-Tang as in COMPARATIVE EXAMPLE 1 (M); (5) 144 mg/kg of STC (Example 3); and (6) the combination of captopril (ACE inhibitor) 1 mg/kg and nifedipine (calcium channel blocker) 0.4 mg/kg (A). The SHR rats in the Western medicine control group (A) had been pre-treated with one week of captopril and nifedipine at the same doses.

Blood pressure and heart rate were monitored continuously throughout the study period. Percent change in the mean arterial blood pressure (maBP) was expressed as the ratio of maBP after treatment to the baseline maBP before treatment. The within-group baseline and post-treatment results were analyzed using the paired Student's T test.

As presented in FIG. 1, all medications showed significant reduction of the blood pressure (indicated with an asterisk, *). However, the root and rhizome of rhubarb alone (H3) was less effective in lowering the blood pressure. Also, the combination of the root of scutellaria and the rhizome of coptis (H 1+2) show a large variation in the blood pressure reduction.

Study 2

Effects of the Herbal Compositions on Maintaining and Controlling Blood Pressure Spontaneous hypertensive rats (SHR) were obtained from the National Experimental Animal Center, Taiwan. The SHR rats were anaesthetized by intraperitoneal injection of urethane at 9 g/kg. The SHR rats were then inserted with a trachea tube, maintained on a respiration apparatus for small animals, and inserted with catheters into the femoral vein and femoral artery.

The catheter from the femoral artery was connected to a pressure transducer, which transmitted the change in pressure to a multi-function recorder for monitoring of the artery blood pressure, mean arterial blood pressure, and heart rate. The femoral vein catheter was in place for intravenous injection. The body temperature of the rats was maintained at 37–38° C. by an electric blanket. The baseline values were recorded for 60 minutes after the blood pressure of the SHR rats were stabilized.

The SHR rats were separated into groups (seven rats per group) and received through gavage daily for two weeks of (1) no treatment (control); (2) 48 mg/kg of composition of COMPARATIVE EXAMPLE 2 (M); (3) 48 mg/kg of STC (Example 3); or (4) the combination of captopril 1 mg/kg and nifedipine 0.4 mg/kg (A). The dosages of M and STC were one-third of those of STUDY 1.

Blood pressure and heart rate were monitored continuously throughout the study period. Values of the mean arterial blood pressure (maBP) and heart rate (HR) were compared on the day after the completion of the 2-week dosing. The between-group results were analyzed using the unpaired Student's T test. The within-group, baseline and post-treatment results were analyzed using paired Student's T test.

Figure 2B:
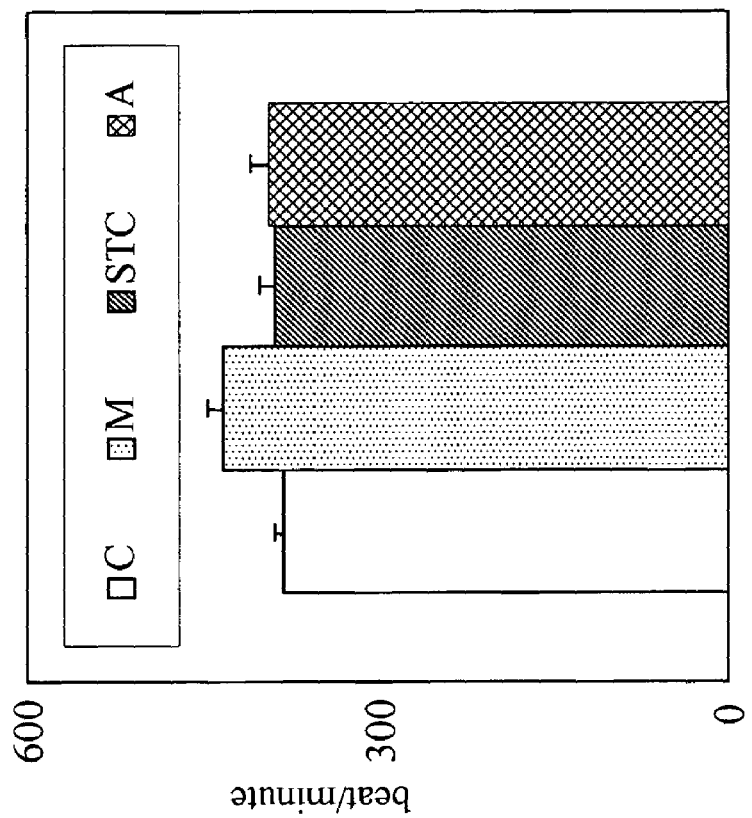
FIGS. 2a and 2b show the effects of: (1) placebo control (C); (2) the modified San-Huang-Hsie-Hsin-Tang decoction as shown in COMPARATIVE EXAMPLE 2 (M), infra; (3) STC (Example 3, infra); and (4) the combination of captopril and nifedipine (A); on mean arterial blood pressure (maBP) and heart rate (HR) of rats, respectively, on the day after a completion of 2-week dose administration.
Figure 2A:
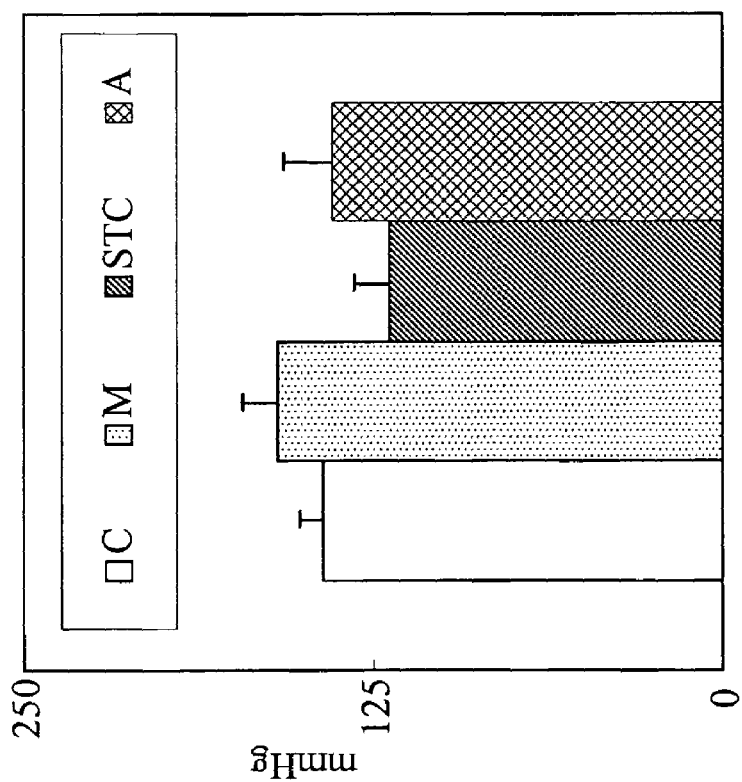

As shown in FIG. 2a, only the group giving STC demonstrated lower and maintained mean arterial blood pressure on the day after the completion of the doses. In contrast, the traditional San-Huang-Hsie-Hsin-Tang decoction (M) and the combination of captopril and nifedipine (A) did not maintain their anti-hypertensive effects on the day after dose completion, despite the multiple dose administration for two weeks.

As shown in FIG. 2b, all three treatments had no effects on the heart rate.

Study 3

Effect of the Herbal Compositions on Preventing Hypertension

The spontaneous hypertension rats (SHR) and normal rats (WKY) younger than 8 weeks old were obtained from the National Experimental Animal Center, Taiwan. Baseline measures of heart rate and blood pressures at the tail are first recorded. The SHR rats were then treated with 14.4 mg/kg/day of the herbal compositions of the present invention as described in the below Example 4 through gavage for one week. The between-group comparison of the baseline measures of the WKY and SHR rats was carried out using the unpaired Student's T test with the statistical significance indicated by an asterisk in the figures. The within-group comparison of the baseline and post-treatment measures of the SHR rats was carried out using paired Student's T test with the statistical significance indicated by an "a" in the figures.

Figure 3B:
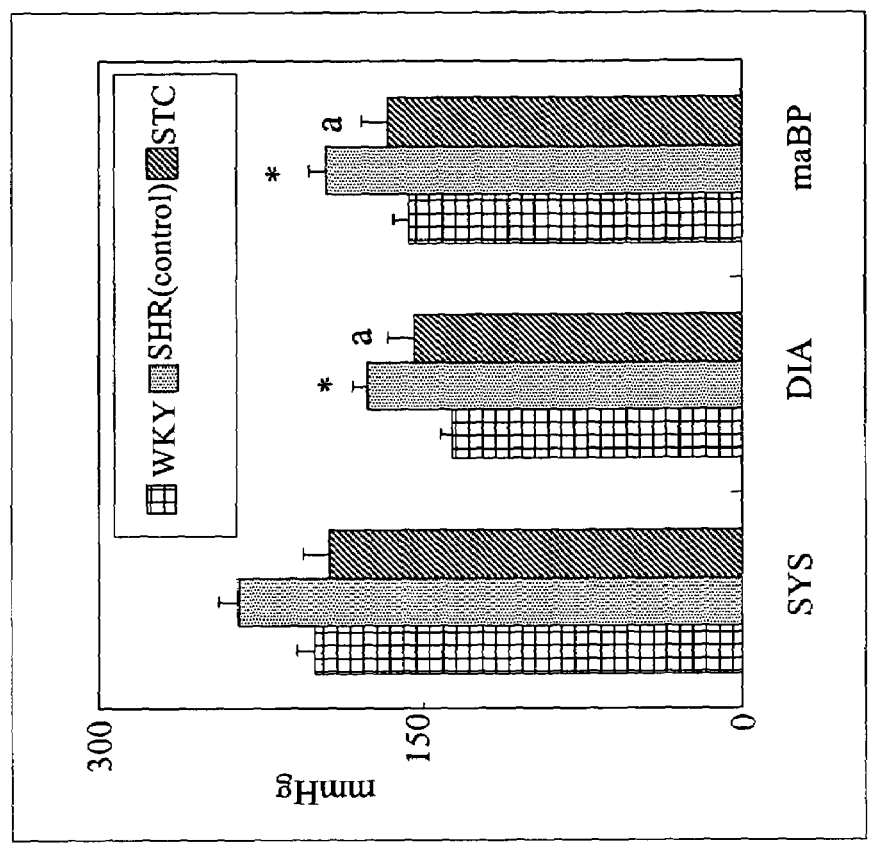
FIGS. 3a and 3b show the effects of STC (Example 3, infra) on heart rate (HR) and blood pressures, respectively, of rats, after the animals were given a daily dose of 14.4 mg/kg for one week. SHR represents the baseline control of the spontaneous hypertensive rats. WKY represents the baseline control of the normal rats. STC were given to the spontaneous hypertensive rats. SYS, DIA, and maBP represent the systolic, diastolic and mean arterial blood pressure, respectively.
Figure 3A:
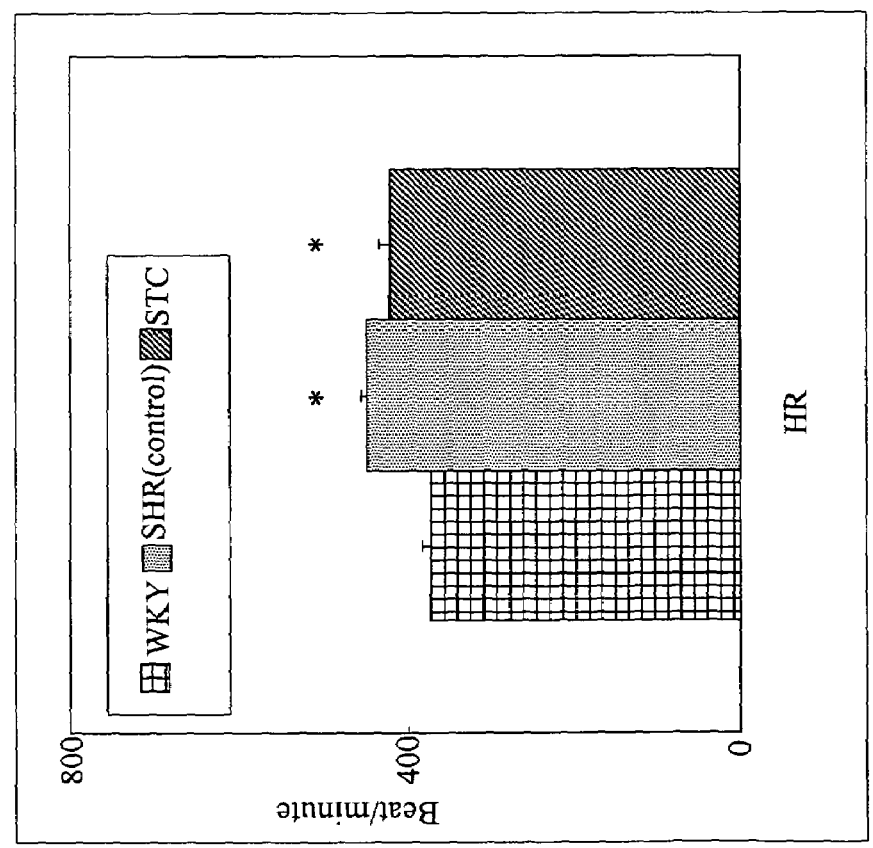

As shown in FIGS. 3a and 3b, the untreated spontaneous hypertensive rats had statistically significantly higher heart rate (HR), systolic pressure (SYS), diastolic pressure (DIA) and mean arterial blood pressure (MED) than the normal rats (WKY). Treatment with the herbal compositions of the present invention (STC) significantly reduced the systolic pressure and mean arterial blood pressure in the spontaneous hypertensive rats (p<0.05, n=5) to levels that were comparable to the normal WKY rats.

Study 4

Effect of the Herbal Compositions on Improving Cardiovascular Conditions in the Elderly Part 1. In Vivo Test Normal WKY rats that were 8 weeks and 10 months of age were used in this study. Baseline blood pressures and heart rate measured at the tails were first recorded for both groups. The 10-month old rats were then treated with one single dose of 48 mg/kg of the herbal compositions of the present invention. Heart rate and blood pressures were measured at 1 hour after the dosing of STC. The between-group comparison of the baseline measures of the 8-week old (Young) and the 10-month old WKY rats (Old) was carried out using the unpaired Student's T test with the statistical significance indicated by an asterisk in the figures. The within-group comparison of the baseline (Old) and post-treatment measures of the 10-week old WKY rats (STC) was carried out using paired Student's T test with the statistical significance indicated by an "a" in the figures.

Figure 4B:
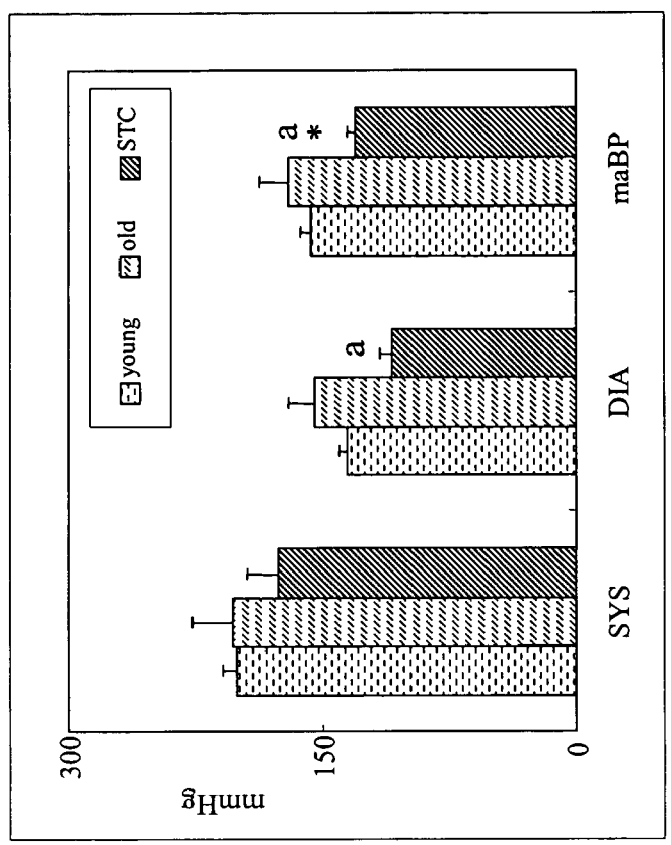
FIGS. 4a and 4b compare the heart rates (HR), and the systolic (SYS), diastolic (DIA) and mean arterial blood pressures (maBP), respectively, in 8-week-old WKY rats (Young), 10-month-old WKY rats (Old) and 10-month-old WKY rats treated with 48 mg/kg of the herbal pharmaceutical composition of the present invention (STC).
Figure 4A:
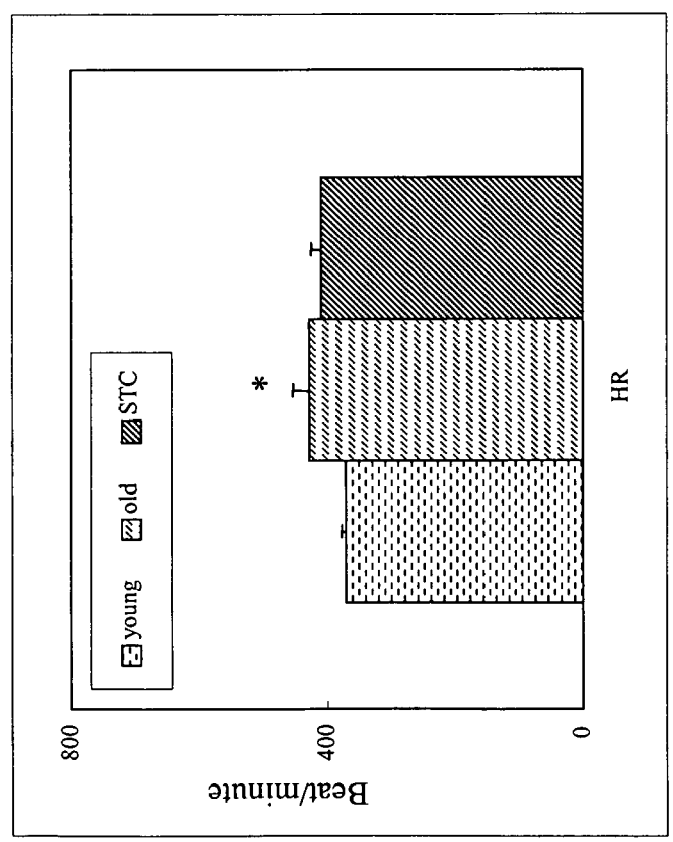

As shown in FIGS. 4a and 4b, the heart rate (HR), diastolic pressure (DIA) and mean arterial blood pressure (maBP) were higher, but not significantly, in the old WKY rats than the young rats. Treatment with the herbal compositions of the present invention (STC) significantly reduce the diastolic pressure and mean arterial blood pressure in the old WKY rats (p<0.05, n=4, indicated with "a" in FIG. 4b) at one hour after the dose administration.

Part 2. Non-Circulation Perfusion Test

Ten-month old SHR rats were anaesthetized by intraperitoneal injection of urethane. The hearts of the anaesthetized rats were removed under assisted respiration. The hearts were immediately inserted with an arterial catheter at the cutting end of the aorta and perfused with 37° C. Krebs-Henselein (KH) buffer at the pressure of 80 cmH$_2$O. The buffer contained 118 mM NaCl, 24.0 mM NaHCO$_3$, 4.7 mM KCl, 1.2 mM KH$_2$PO$_4$, 1.2 mM MgSO$_4$, 1.7 mM CaCl$_2$, and 10.0 mM glucose continuously gassed with the mixture of 95% O$_2$ and 5% CO$_2$.

The isolated hearts were perfused for 15 minutes with the KH buffer and then with the KH buffer containing the herbal compositions of the present invention (STC) for 15 minutes, reaching a steady state. The coronary flow and coronary perfusion pressure (CPP) were measured (1) before the perfusion of STC, (2) after the perfusion of STC, and (3) after reperfusion with STC for 60 minutes post L-phenylephrine-induced ischemia. The results indicated that perfusion with the herbal compositions of the present invention as described in the below Example 4 could improve the reduction in the coronary flow that was induced by 10 mM L-phenylephrine from 12.6 mL/min to 13.2 mL/min. This suggested the herbal pharmaceutical compositions of the present invention was effective in improving cardiovascular conditions.

Study 5

Effects of the Herbal Compositions in Inhibiting the Enzyme Formations and Activities of iNOS and COX-2

The mouse macrophage cell line RAW 264.7 was used in this study. The mouse macrophage cells were treated with lipopolysaccharide (LPS) and various amounts of the herbal compositions of the present invention for 12 hours. LPS is known to induce the syntheses of the enzymes, iNOS and COX-2 in the mouse macrophage cells. The treated macrophage cells were first detached from the cultural plates by repeated flush using micropipett. The cell mixtures were then harvested and centrifuged at 2000 rpm. The clear supernatants were collected and assayed for the content of nitrile using the Griess Test Reagent and for the content of $PGE_2$ using the ELISA method. The pellets formed after the centrifugation were mixed with the Lysis buffer and homogenized. The resultant mixtures were assayed for protein content. A 30-μg aliquot of the homogenized mixture was placed on the polyacrylamide gel to separate the proteins by electrophoresis. Proteins on the developed polyacrylamide gel were then transferred onto the polyvinylidene difluoride (PVDF) membrane and detected with the antibodies for iNOS and COX-2.

Figure 5:
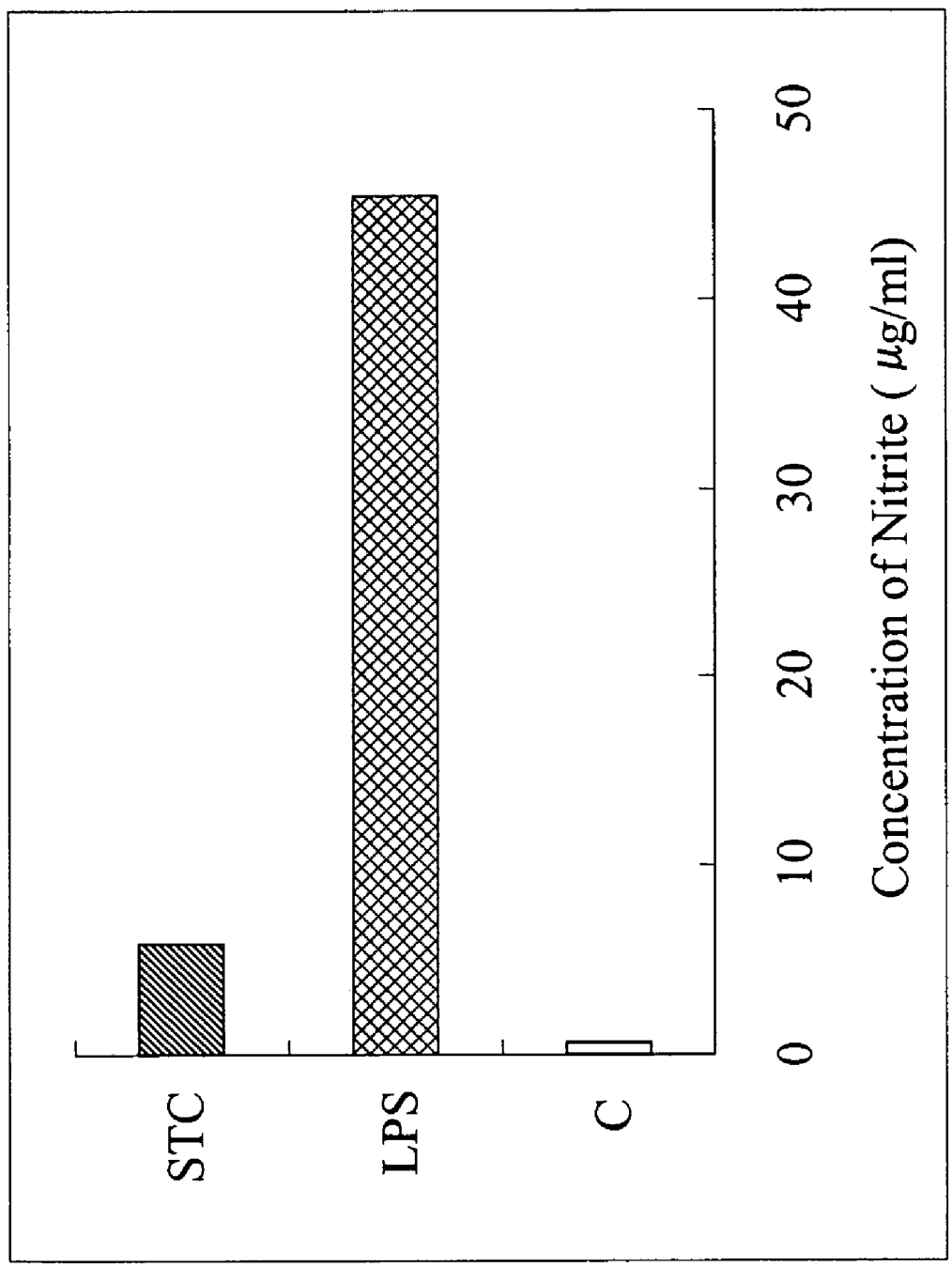
FIG. 5 shows inhibition of nitrite formation in the mouse macrophage cell line RAW 264.7 by STC. The symbol, C, represents the untreated control mouse macrophage cells. LPS and STC represent the mouse macrophage cells treated with lipopoly-saccharide and the herbal pharmaceutical composition of the present invention, respectively.
Figure 6:
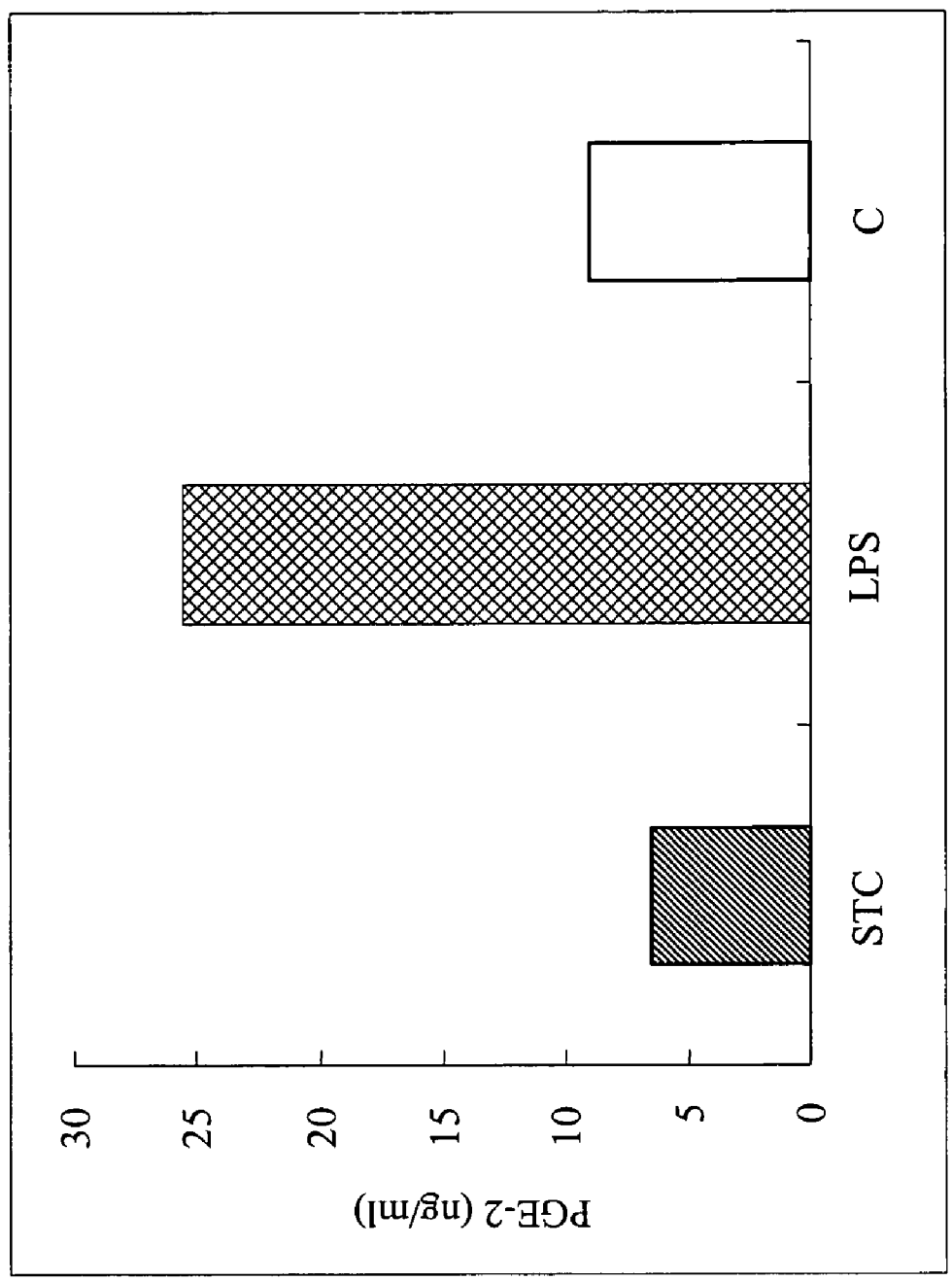
FIG. 6 shows the inhibitory effects of the herbal pharmaceutical composition of the present invention on PEG-2 formation by mouse macrophage cell line RAW 264.7. LPS and STC represent the mouse macrophage cells treated with lipopolysaccharide and 10 mg/mL of the herbal pharmaceutical composition of the present invention.

The results showed that the herbal compositions of the present invention was effective in inhibiting the formation of the nitrile (FIG. 5) by inhibiting the protein synthesis of iNOS. The herbal compositions of the present invention inhibited the formation of $PEG_2$, the end product of COX-2 (FIG. 6), but not the protein synthesis of the enzyme itself, suggesting that the herbal compositions of the present invention might possess anti-inflammatory activity by inhibiting the activity of COX-2.

Study 6

Effect of the Herbal Compositions on Inhibition of iNOS and COX-2 Protein Biosynthesis Sprague Dawley (SD) rats and the spontaneous hypertensive (SHR) rats were used in this study. The hearts from lipopolysaccharide-treated SD rats and the lungs from SHR rats treated with the herbal compositions of the present invention and other control groups were removed from the animals. Small portions of the isolated organs were first ground in mortars containing liquid nitrogen and then homogenized in the Lysis buffer.

Aliquots of the resultant mixtures were assayed for protein contents. Another 30-μg aliquots of the resultant mixtures were placed on the polyacrylamide gel to separate the proteins by electrophoresis. Proteins on the developed polyacrylamide gel were then transferred onto the polyvinylidene difluoride (PVDF) membrane and detected with the antibodies for iNOS and COX-2.

Figure 7A:
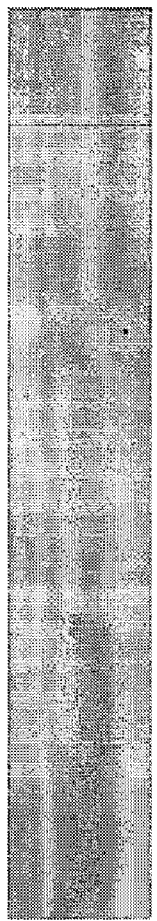
FIGS. 7a and 7b show inhibition on the protein syntheses of COX-2 and iNOS, respectively, by the herbal pharmaceutical composition of the present invention (STC). Column 1 presents the enzymes isolated from the heart of spontaneous hypertensive rats treated with 20 mg/kg of lipopolysaccharide. Column 2 presents the enzymes isolated from the lungs of spontaneous hypertensive rats treated with the herbal pharmaceutical composition of the present invention. Column 3 presents the enzymes isolated from the lungs of the control, untreated spontaneous hypertensive rats.
Figure 7B:
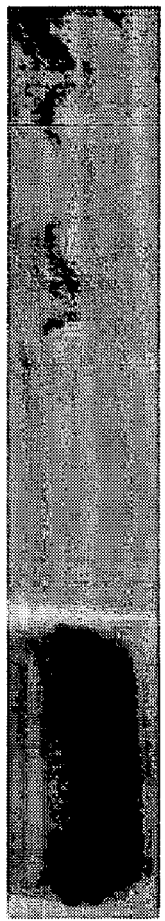

The results showed that intraperitoneal treatment of 20 mg/kg LPS induced inflammatory responses in the SD rats. The SD rats showed symptoms of abdominal pain and writhing. As shown in FIGS. 7a and 7b, formations of the COX-2 and iNOS proteins, respectively, were highest in the hearts of the SD rats (Column 1), then followed by the lungs of the untreated SHR rats (Column 3). STC (Example 3) clearly inhibited the formation of the COX-2 and iNOS proteins in the SHR rats (Column 2).

Study 7

Effect of the Herbal Compositions on Inhibition of iNOS Gene Expression

The spontaneous hypertensive (SHR) rats were treated with (1) the pharmaceutical compositions of the present invention, STC (S); (2) western medicine; or (3) control. Lungs from the animals were removed and tissue RNA was extracted using Trizol. The concentrations and ratios of the extracted RNA were determined using the spectrometer. The cDNA was then prepared from 1-μg aliquot of RNA by reverse transcription. A 2-μL of the cDNA solutions was mixed with the iNOS primer and multiplied using the polymerase chain reaction (PCR) method. The resultant DNA mixtures were run through the agarose gel for DNA separations.

Figure 8B:
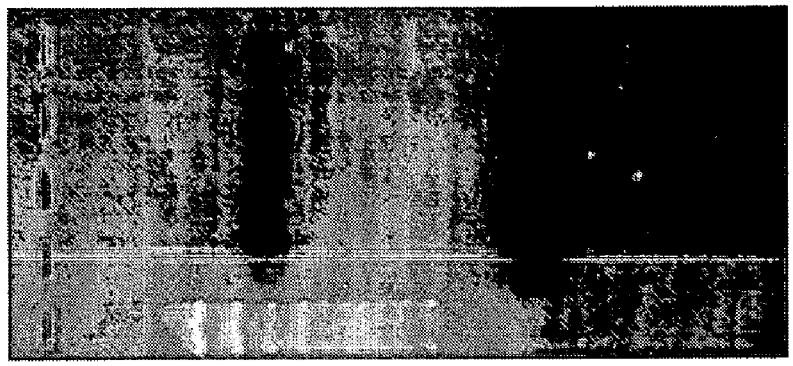
FIGS. 8a and 8b show RNA expressions of β-actin and iNOS, respectively, in the lung of spontaneous hypertensive rats that were treated with (1) the modified San-Huang-Hsie-Hsin-Tang decoction (M) (cDNA marker), (2) STC (Example 3, infra) (S), (3) control (C), and (4) a combination of captopril and nifedipine (A).
Figure 8A:
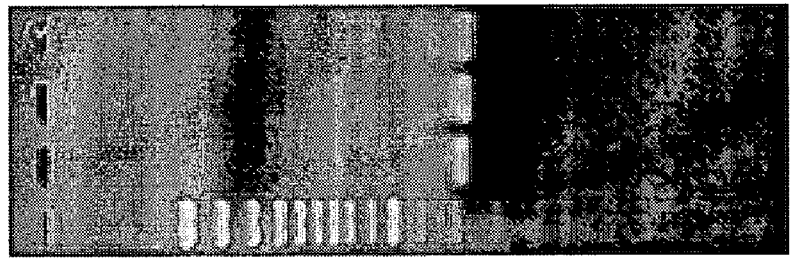

As indicated in 8a, detection of the β-actin cDNA on the agarose gel indicated the RNA extraction process was properly carried out. As shown in FIG. 8b, the DNA bands was clearly seen in the western medicine group (A), less obvious in the control (untreated) group (C) and not observed for the SHR rats treated with the herbal compositions of the present invention (S). This suggested that the herbal compositions of the present invention could inhibit the expression of iNOS in SHR rats.

Study 8

Effect of the Herbal Compositions on Reduction of CRP

The spontaneous hypertensive rats were treated with 48 mg/kg of STC (Example 3) for 2 weeks. After the conclusion of the oral dose administration, blood samples were collected from both the control (untreated) rats and the STC-treated rats. Plasma samples were prepared from the blood samples by high-speed centrifugation and then assayed for the CRP contents using ELISA.

Figure 9:
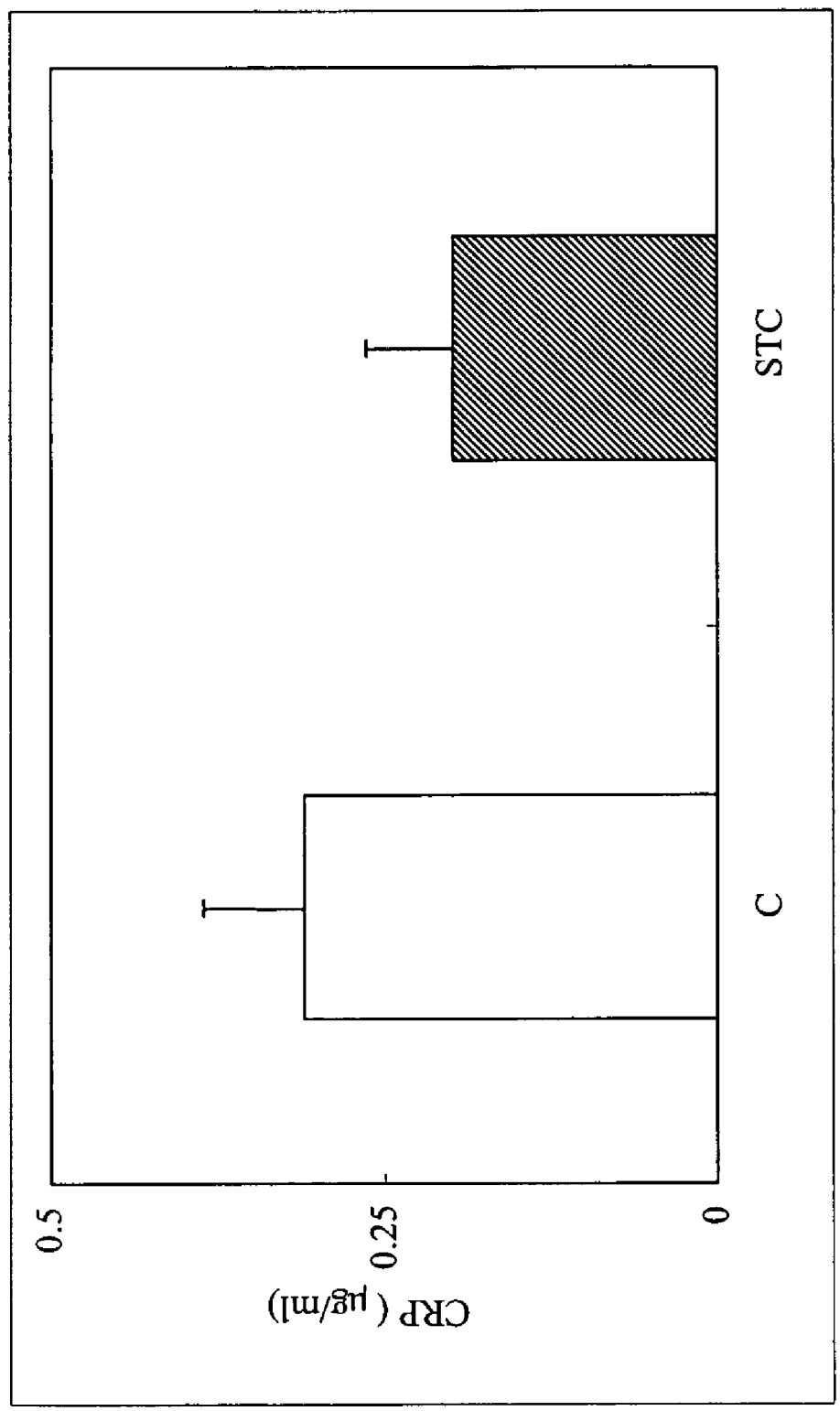
FIG. 9 shows the ELISA analysis of CRP in the blood of spontaneous hypertensive rats of the control group (C) and the group treated with 48 mg/kg of STC (Example 3, infra) for two weeks.

As indicated in FIG. 9, the herbal pharmaceutical compositions of the present invention was effective in reducing CRP formation in the spontaneous hypertensive rats.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A method for treating patients with hypertension and/or ischemia comprising:

administering an effective amount of an herbal pharmaceutical composition to said patients; wherein said herbal pharmaceutical composition comprising:

an extract of Radix Scutellariae (root of scutellaria);

an extract of Rhizoma Coptidis (rhizome of coptis);

an extract of Radix et Rhizoma Rhei (root and rhizome of rhubarb);

and dry powder of Radix Ginseng (root of ginseng) or Radix Panacis Quinquefolii (American ginseng);

wherein said extract of said root of scutellaria, said extract of said rhizoma of coptis, and said extract of said root and rhizome of rhubarb are produced by extracting said root of scutellaria, said rhizoma of coptis, said root and rhizome of rhubarb by a solvent which is at least one selected from the group consisting of water and alcohol.

2. The method according to claim 1, wherein said herbal pharmaceutical composition is orally administered to patients.

3. The method according to claim 1, wherein said herbal pharmaceutical composition is used to lower blood pressure or maintain stable blood pressure in said patients.

\* \* \* \* \*